United States Patent [19]

Traber et al.

[11] 4,220,641
[45] Sep. 2, 1980

[54] ORGANIC COMPOUNDS

[75] Inventors: René P. Traber; Max Kuhn, both of Basel; Hans Hofmann, Ettingen; Eugen Häri, Therwil, all of Switzerland

[73] Assignee: Sandoz Ltd., Basel, Switzerland

[21] Appl. No.: 902,794

[22] Filed: May 4, 1978

[30] Foreign Application Priority Data

May 10, 1977 [CH] Switzerland .......................... 5822/77
May 10, 1977 [CH] Switzerland .......................... 5823/77
Jun. 17, 1977 [CH] Switzerland .......................... 7457/77

[51] Int. Cl.² .................... A61K 37/00; C07C 103/52
[52] U.S. Cl. ............................. 424/177; 260/112.5 R
[58] Field of Search ................. 424/177; 260/112.5 R

[56] References Cited
PUBLICATIONS

A. Rüegger et al., Hel. Chim. Acta 59, 1976, 1075–1093.
T. J. Petcher et al., Hel. Chim. Acta 59, 1976, 1480–1489.

Primary Examiner—Delbert R. Phillips
Attorney, Agent, or Firm—Gerald D. Sharkin; Robert S. Honor; Thomas O. McGovern

[57] ABSTRACT

The present invention relates to cyclosporin derivatives, especially compounds of formula I

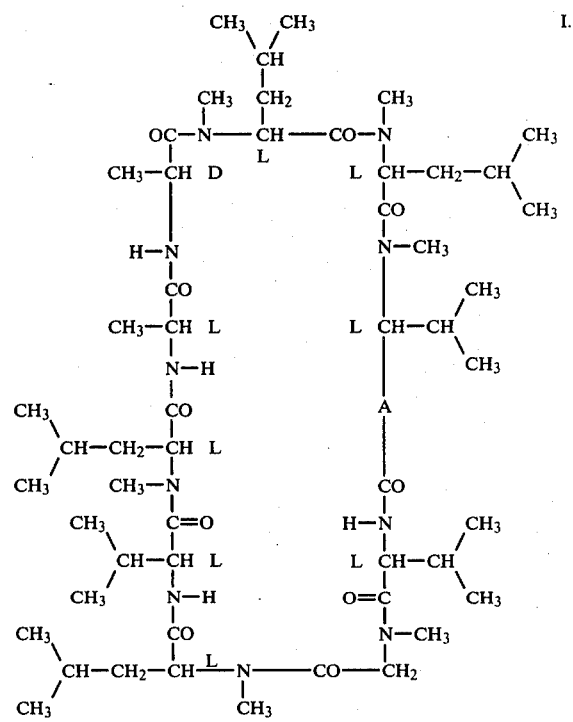

wherein A is

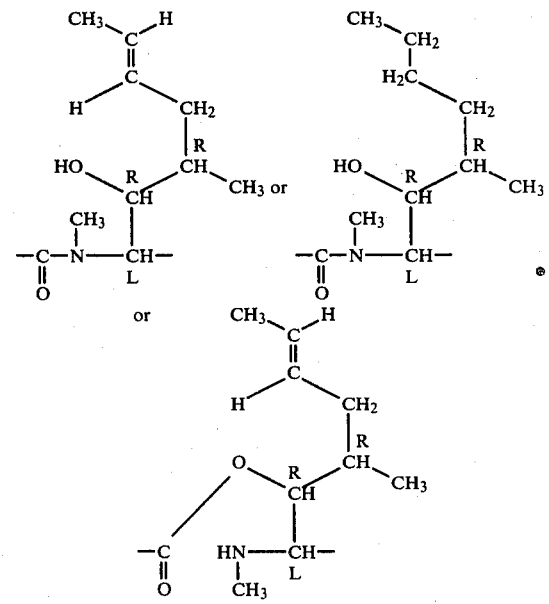

useful as anti-arthritic agents.

10 Claims, No Drawings

ORGANIC COMPOUNDS

IMPROVEMENTS IN OR RELATING TO ORGANIC COMPOUNDS

The present invention relates to cyclosporin derivatives, especially compounds of formula I

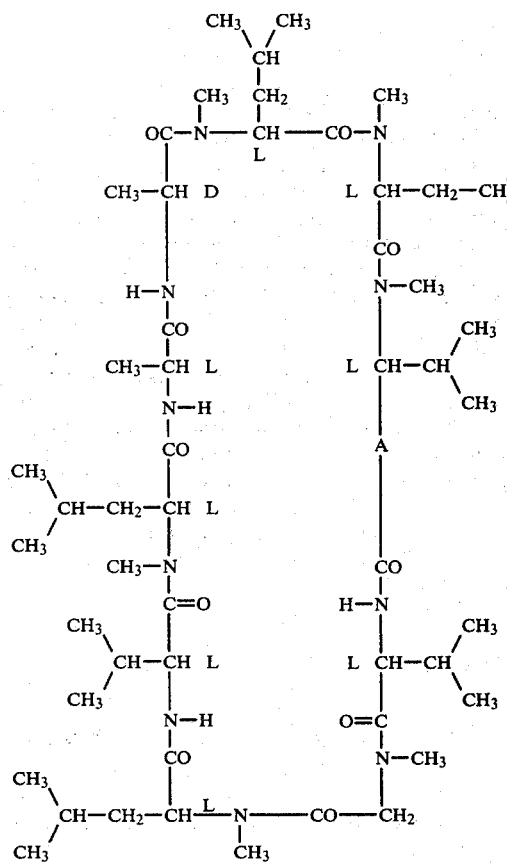

wherein A is

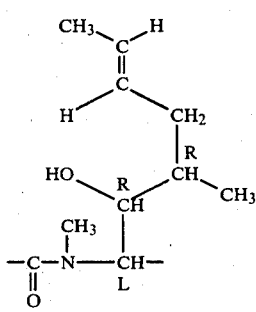

or

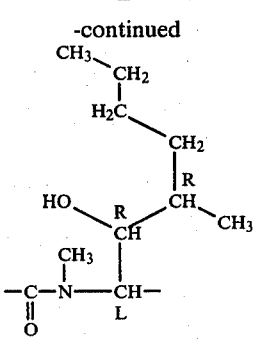

or

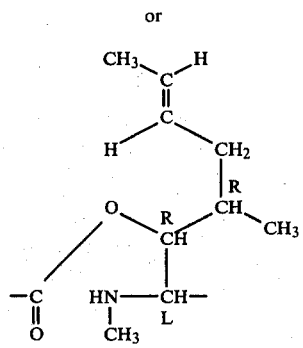

hereinafter referred to as cyclosporin D, dihydrocyclosporin D or isocyclosporin D, respectively.

The present invention provides a process for the production of:

(a) cyclosporin D which comprises cultivating a cyclosporin D producing strain of the species Tolypocladium inflatum Gams in the presence of a nutrient medium and isolating cyclosporin D, (b) dihydrocyclosporin which comprises hydrogenating cyclosporin D, or (c) isocyclosporin D which comprises rearranging cyclosporin D under acidic conditions.

The cultivation process (process a) may be effected in conventional manner for analogous strains, e.g. as described in Example 1 hereinafter.

A preferred cyclosporin D producing strain is the freely available strain NRRL 8044 of the species Tolypocladium inflatum Gams, a culture of which is available from United States Department of Agriculture (Northern Research and Development Division), Peoria, Ill., USA. This strain was formerly described as a strain of the species Trichoderma polysporum (Link ex Pers.) and is described in the literature, e.g. in DOS No. 2,455,859.

Alternatively cyclosporin D producing strains obtained by selection or mutation of NRRL 8044, or treatment of this strain by ultraviolet light or x-rays, or treatment of this strain with laboratory chemicals, may be used.

Cyclosporin D may be isolated in conventional manner, e.g. as described in Example 1, from other natural products that may be produced in greater amounts, e.g. the somewhat more polar cyclosporin A (also known as S 7481/F-1), the more polar cyclosporin B (also known as S 7481/F-2) and the yet more polar cyclosporin C.

The hydrogenation process (process b) may be effected in conventional manner, e.g. by catalytic hydrogenation. Suitable solvents include methanol, ethanol, isopropanol or ethyl acetate. The process is conveniently effected in a neutral medium at a temperature between 20° and 30° C. and at atmospheric or slightly elevated pressure. A suitable catalyst is palladium on charcoal.

The acid treatment of process c may be effected in conventional manner, e.g. with trifluoroacetic acid or preferably methanesulphonic acid or p-toluenesulphonic acid. The mole ratio of acid to cyclosporin D is preferably between 1:1 and 4:1. Suitable solvents include methanol, chloroform, and dioxane. Suitable temperatures are between 20° and 65° C., preferably 40° to 55° C.

In the following examples all temperatures are in degrees Centigrade. All ratios are by volume unless otherwise stated.

EXAMPLE 1: CYCLOSPORIN D 500 liters of a nutrient solution containing per liter, 40 g of glucose, 2 g of sodium caseinate, 2.5 g of ammonium phosphate, 5 g of $MgSO_4.7H_2O$, 2 g of $KH_2PO_4$, 3 g of $NaHO_3$, 0.5 g of KCl, 0.01 g of $FeSO_4$ and demineralized water to 1 liter, are inoculated with 50 liters of a pre-culture of the strain NRRL 8044 and are incubated in a steel fermenter under stirring (170 rpm) and aeration (1 liter air/minute/liter nutrient solution) for 13 days at 27° (see published German Patent Application 2 455 859).

The culture liquor is stirred with the same amount of n-butyl acetate, concentrated by evaporation in a vacuum after separation of the organic phase and the crude extract is de-fatted by a 3-stage partition between methanol/water (9:1) and petroleum ether. The methanolic phase is separated, concentrated by evaporation in a vacuum and the crude product is precipitated by the addition of water. The material obtained upon filtration is chromatographed on silica gel with hexane/acetone (2:1) as eluant. The initially eluted fractions contain predominantly cyclosporin A and cyclosporin D and the later eluted fractions contain predominantly cyclosporin C. For further purification the cyclosporin A-and D-containing fractions are crystallized from a 2- to 2.5-fold amount of acetone at −15°. The crystallate is further chromatographed twice on silica gel, the fractions initially eluted with water-saturated ethyl acetate, containing cyclosporin D in greatly enriched form. These are dissolved in twice the amount of acetone and are allowed to crystallize at −15°. The resulting crude crystalline product of cyclosporin D is dissolved for further purification in a 10-fold amount of acetone, 2% by weight of active charcoal are added and heating is effected for 5 minutes to 60°. The clear and almost colourless filtrate obtained upon filtration over talc is concentrated by evaporation to a third of its volume and is allowed to cool down at room temperature, whereupon cyclosporin D crystallizes spontaneously. The crystallization is completed by allowing to stand at −17°. The crystals obtained by filtration are washed with a small amount of ice-cold acetone and are subsequently dried in a high vacuum at 80° C. for 2 hours.

CHARACTERIZATION OF cyclosporin D
Colourless, prismatic crystals. M.P. 148°–151°
$[\alpha]_D^{20} = -245°$ (c=0.52 in chloroform)
$[\alpha]_D^{20} = -211°$ (c=0.51 in methanol)

EXAMPLE 2: DIHYDROCYCLOSPORIN D 400 mg of palladium on charcoal [10% (w/w) palladium] are pre-hydrogenated in 15 ml of ethanol during the course of 20 minutes. To this suspension of the palladium catalyst, there is added the solution of 3.66 g of cyclosporin D in 30 ml of ethanol. The mixture is hydrogenated at 24° and at a pressure of 736 mm of Hg until the hydrogen up-take is complete. Subsequently the catalyst is filtered off and the filtrate is evaporated to dryness in a vacuum at 20° to 40°. The dihydrocyclosporin D, which is pure by thin layer chromatography, precipitates as colourless amorphous powder, which is dried in a high vacuum for 4 hours at 70°.

CHARACTERIZATION OF dihydrocyclosporin D:
M.P. 153°–156°
$[\alpha]_D^{20} = -237°$ (c=0.56 in chloroform)
$[\alpha]_D^{20} = -196°$ (c=0.58 in methanol)

EXAMPLE 3: isocyclosporin D

A solution of 3.6 g of methanesulphonic acid in 60 ml of dioxane is added to the solution of 18.25 g of antibiotic cyclosporin D in 120 ml of absolute dioxane and the mixture is kept at 50° in the absence of moisture. The reaction course is followed by thin layer chromatography [polygram SIL G-foils; chloroform/methanol/glacial acetic acid (90:6:4); iodine vapour for detection]. After 17 hours, the mixture is cooled to room temperature. After 3.38 g of anhydrous sodium acetate is added the precipitated salt is filtered with suction after stirring for 15 minutes and the filtrate is concentrated by evaporation in a vacuum at 45°. The 21 g of residue are chromatographed on 1.5 kg of silica gel, using chloroform/methanol (98:2) for elution. The fractions consisting of practically pure iso-cyclosporin D are combined, concentrated by evaporation in a vacuum at 50° and the residue is crystallized twice to thrice from ether, whereupon the isocyclosporin D precipitates out.

CHARACTERIZATION OF isocyclosporin D:
M.P. 142°–144°
$[\alpha]_D^{20} = -205.5°$ (c=0.51 in chloroform)
$[\alpha]_D^{20} = -144.4°$ (c=0.64 in methanol)

The compounds of formula I exhibit pharmacological activity. In particular the compounds exhibit anti-inflamatory activity and anti-arthritic activity as indicated by an inhibition of swellings in the freunds adjuvant arthritis test in rats on p.o. administration of 3 to 100 mg/kg of the compounds.

The compounds are therefore useful for the treatment and prophylaxis of chronic inflammations, e.g. arthritis and rheumatic disorders.

Furthermore, cyclosporin D and dihydrocyclosporin D exhibit immuno-suppressure activity, e.g. by their effect on humonal and cellular immunity, as indicated in standard tests, e.g.

(a) in the lymphocyte stimulation test according to Janossy in vitro at concentrations of 0.01 to 10.0 µg/ml a strong inhibition of $H^3$-thymidine incorporation, of the proliferation rate and of the blastogenese of mice spleen lymphoctyes stimulated with Concanavalin A was ascertained.

(b) Oxazolon test in mice:

A decrease in the ear swelling is observed upon administration of 5×70 mg/kg p.o. of the compound.

For all these uses the dosage will, of course, vary depending on the compound employed, mode of administration and treatment desired. However, in general, satisfactory results are obtained when administered at a daily dosage of from about 1 mg to about 200 mg per kg animal body weight, conveniently given in divided doses 2 to 4 times a day or in sustained release form. For the larger mammals, the total daily dosage is in the range from about 50 to about 900 mg, and dosage forms suitable for oral administration comprise from about 15 mg to about 450 mg (e.g. 25-300 mg) of the compounds admixed with a solid or liquid pharmaceutical carrier or diluent.

The present invention also provides a pharmaceutical composition comprising a compound of formula I in association with a pharmaceutical carrier or diluent.

Such compositions may be in the form of, for example, a solution or a tablet.

The compound of example 3 exhibits especially interesting activity.

What we claim is:

1. A compound closen from cyclosporin D, dihydrocyclosporin D or isocyclosporin D.
2. The compound of claim 1 which is cyclosporin D.
3. The compound of claim 1 which is dihydrocyclosporin D.
4. The compound of claim 1 which is isocyclosporin D.
5. A pharmaceutical composition useful in treating chronic inflammations or immunosuppressant disorders comprising a therapeutically effective amount of a compound of claim 1 in association with a pharmaceutical carrier or diluent.
6. The pharmaceutical composition according to claim 5 in which the compound is isocyclosporin D.
7. A method of treating chronic inflammations or immuno-suppressive disorders in animals, which comprises administering a therapeutically effective amount of a compound of claim 1 to an animal in need of such treatment.
8. The method of claim 7 in which the compound is isocyclosporin D.
9. A method according to claim 8 in which from 50 to 900 milligrams of the compound are administered daily.
10. A method according to claim 8 in which from 15 to 450 milligrams of the compound are administered orally in unit dosage form.

* * * * *

UNITED STATES PATENT AND TRADEMARK OFFICE
CERTIFICATE OF CORRECTION

PATENT NO. : 4,220,641
DATED : September 2, 1980
INVENTOR(S) : Rene P. Traber/Max Kuhn/Hans Hofmann/Eugen Harri It is certified that error appears in the above—identified patent and that said Letters Patent is hereby corrected as shown below:

Title page, left-hand column in the heading "Inventors", the fourth-named inventor, "Häri" should read --Härri--.

Signed and Sealed this

Eleventh Day of May 1982

[SEAL]

Attest:

Attesting Officer

GERALD J. MOSSINGHOFF
Commissioner of Patents and Trademarks